US011798666B1

(12) United States Patent
Chmil et al.

(10) Patent No.: US 11,798,666 B1
(45) Date of Patent: Oct. 24, 2023

(54) COMPUTING SYSTEM FOR REDIRECTING REFILLS ON AN ELECTRONIC PRESCRIPTION

(71) Applicant: Allscripts Software, LLC, Raleigh, NC (US)

(72) Inventors: Igor Chmil, Buffalo Grove, IL (US); Stanislav Makarskyy, Arlington Heights, IL (US); Nikhil Rajeev Joshi, Pune (IN); Anu Jindal, Naperville, IL (US)

(73) Assignee: Allscripts Software, LLC, Raleigh, NC (US)

( * ) Notice: Subject to any disclaimer, the term of this patent is extended or adjusted under 35 U.S.C. 154(b) by 0 days.

(21) Appl. No.: 17/462,249

(22) Filed: Aug. 31, 2021

Related U.S. Application Data

(63) Continuation of application No. 16/003,050, filed on Jun. 7, 2018, now Pat. No. 11,114,191.

(51) Int. Cl.
*G16H 20/10* (2018.01)
*G16H 10/60* (2018.01)

(52) U.S. Cl.
CPC ............ *G16H 20/10* (2018.01); *G16H 10/60* (2018.01)

(58) Field of Classification Search
CPC .... G16H 10/00–80/00; G06F 1/00–2221/2153
See application file for complete search history.

(56) References Cited

U.S. PATENT DOCUMENTS

| 8,180,653 | B2* | 5/2012 | Banfield | G06Q 10/10 |
| | | | | 705/3 |
| 10,025,907 | B1* | 7/2018 | Parker, Jr. | G16H 20/10 |
| 10,235,729 | B1* | 3/2019 | Cedergreen | G16H 40/20 |
| 10,366,784 | B1* | 7/2019 | Eller | G16H 10/60 |

(Continued)

FOREIGN PATENT DOCUMENTS

WO  WO200137138  *  5/2001

OTHER PUBLICATIONS https://web.archive.org/web/20171210031208/https://learn.pcc.com/help/enroll-prescribe-epcs/,"EPCS:HowtoEnrollPrescribers andPrescribe—PCCLearn," pp. 1-35. (Year: 2017).*

*Primary Examiner* — Jonathon A. Szumny
(74) *Attorney, Agent, or Firm* — Calfee, Halter & Griswold LLP

(57) ABSTRACT

A computing system for redirecting electronic prescription refills is disclosed herein. A server computer device executing an electronic health records application constructs an electronic prescription for a patient and causes the electronic prescription to be routed to a first pharmacy device of a first pharmacy. The electronic prescription includes at least one refill. Subsequently, the server computing device receives an identifier for the electronic prescription and an identifier for a second pharmacy from a second server computing device executing a patient portal application, wherein the identifier for the second pharmacy is specified by the patient. The server computing device identifies the electronic prescription, determines a number of refills remaining on the electronic prescription, and constructs a second electronic prescription including the number of refills. The server computing device then causes the second electronic prescription to be routed to a second pharmacy device of the second pharmacy.

20 Claims, 8 Drawing Sheets

(56) References Cited

U.S. PATENT DOCUMENTS

| | | | | |
|---|---|---|---|---|
| 10,373,255 B1* | 8/2019 | Cedergreen | | G16H 20/10 |
| 2004/0260577 A1* | 12/2004 | Dahlin | | G16H 50/20 |
| | | | | 705/2 |
| 2006/0259330 A1* | 11/2006 | Schranz | | G06Q 10/10 |
| | | | | 235/487 |
| 2007/0219825 A1* | 9/2007 | Maetzold | | G16H 20/10 |
| | | | | 707/999.102 |
| 2008/0126135 A1* | 5/2008 | Woo | | G06Q 10/06 |
| | | | | 705/3 |
| 2010/0057489 A1* | 3/2010 | Howe | | G06Q 20/102 |
| | | | | 705/40 |
| 2010/0063836 A1* | 3/2010 | Ballard | | G16H 80/00 |
| | | | | 705/2 |
| 2011/0082705 A1* | 4/2011 | Kobylevsky | | G06Q 10/10 |
| | | | | 705/2 |
| 2011/0161109 A1* | 6/2011 | Pinsonneault | | G06Q 40/08 |
| | | | | 705/2 |
| 2011/0173020 A1* | 7/2011 | Bailey | | G06Q 10/10 |
| | | | | 382/218 |
| 2013/0231945 A1* | 9/2013 | Barry | | G16H 40/67 |
| | | | | 705/2 |
| 2014/0236635 A1* | 8/2014 | Liberty | | G16H 10/60 |
| | | | | 705/3 |
| 2014/0278495 A1* | 9/2014 | Rourke | | G06Q 10/06315 |
| | | | | 705/2 |
| 2015/0161351 A1* | 6/2015 | Scalpati | | G16H 10/60 |
| | | | | 705/2 |
| 2015/0213204 A1* | 7/2015 | Bose | | G16Z 99/00 |
| | | | | 705/3 |
| 2015/0242592 A1* | 8/2015 | Weiss | | G16H 20/10 |
| | | | | 705/2 |
| 2015/0371001 A1* | 12/2015 | Pinsonneault | | G16H 20/10 |
| | | | | 705/2 |
| 2016/0210434 A1* | 7/2016 | Al-Sharif | | G16H 50/30 |
| 2017/0169186 A1* | 6/2017 | Tumma | | G16H 20/10 |
| 2017/0213010 A1* | 7/2017 | Sucilla | | G16H 20/10 |
| 2017/0300627 A1* | 10/2017 | Giordano | | G06F 21/6245 |
| 2017/0337346 A1* | 11/2017 | Goel | | G16H 40/20 |
| 2018/0121620 A1* | 5/2018 | Bastide | | G06F 16/334 |
| 2018/0253682 A1* | 9/2018 | Gilman | | G06Q 20/28 |
| 2019/0095582 A1* | 3/2019 | Waits | | G16H 10/60 |
| 2019/0096522 A1* | 3/2019 | Scriber | | G16H 40/20 |
| 2019/0362828 A1* | 11/2019 | Laxer | | H04L 63/083 |
| 2020/0135317 A1* | 4/2020 | Karbowicz | | G16H 20/10 |

* cited by examiner

COMPUTING SYSTEM FOR REDIRECTING REFILLS ON AN ELECTRONIC PRESCRIPTION

RELATED APPLICATION

This application is a continuation of U.S. patent application Ser. No. 16/003,050, filed on Jun. 7, 2018, and entitled, "COMPUTING SYSTEM FOR REDIRECTING REFILLS ON AN ELECTRONIC PRESCRIPTION", the entirety of which is incorporated herein by reference.

BACKGROUND

Electronic health record applications (EHRs) are computer-executable applications utilized in healthcare environments. EHRs are generally configured to perform various tasks related to healthcare including patient intake tasks, insurance processing tasks, billing tasks, health record maintenance tasks, and so forth. Some EHRs have been configured with electronic prescription functionality, where an EHR can receive input from a healthcare worker causing the EHR to create an electronic prescription for a medication for a patient, and the EHR can be configured to direct the electronic prescription to a pharmacy specified by the healthcare worker and/or the patient. A device operated by the pharmacy (e.g., a computing device) can receive the electronic prescription from the EHR, and the device can notify a pharmacist at the pharmacy that the prescription is to be filled. The pharmacist may then fill the prescription.

An electronic prescription may include refills, whereby the electronic prescription can be refilled by the pharmacy a certain number of times without further approval by the healthcare worker that prescribed the medication. For instance, the electronic prescription may be for a one-year supply of the medication, and the electronic prescription may indicate that refills are available in one-month intervals.

Due to changing circumstances (e.g., moving to a new residence, change in pharmacy preference, etc.) of a patient, it may be desirable to change the pharmacy that fills the electronic prescription midway through a lifetime of the electronic prescription. For instance, the patient may want to have the electronic prescription filled at a first pharmacy for an initial fill and the first three refills, but may subsequently decide that the electronic prescription is to be filled by a second pharmacy for the remaining eight refills.

Conventionally, in order to redirect refills on the (existing) electronic prescription to the second pharmacy, the patient must contact the healthcare worker that prescribed the electronic prescription and must provide the healthcare worker with an identifier for the second pharmacy to which refills of the electronic prescription are to be routed. The EHR must then receive manual input (by way of a client EHR exiting on a client computing device operated by the healthcare worker) from the healthcare worker causing the EHR to redirect refills on the electronic prescription to the second pharmacy specified by the patient. This leads to an inefficient use of client computing resources. Alternatively, the patient may contact the first pharmacy, and the first pharmacy may contact the healthcare worker that prescribed the medication. Thus, conventional EHRs are not well-suited for redirecting refills on an existing electronic prescription from a first pharmacy to a second pharmacy.

SUMMARY

The following is a brief summary of subject matter that is described in greater detail herein. This summary is not intended to be limiting as to the scope of the claims.

Described herein are various technologies pertaining to redirection of refills on electronic prescriptions to different pharmacies. More specifically, an electronic health records application (EHR) is described herein, wherein the EHR is a distributed application that includes server-side functionality (server EHR) and client-side functionality (client EHR). A patient portal application is also described herein, wherein the patient portal application is a distributed application that includes server-side functionality (server patient portal application) and client-side functionality (client patient portal application). The EHR and the patient portal application can work in conjunction with one another to redirect remaining refills on an existing electronic prescription for a patient from a first pharmacy to a second pharmacy specified by the patient.

In operation, a client computing device executing the client EHR is operated by a healthcare worker providing care to a patient. The healthcare worker may decide to prescribe a medication to the patient. The client EHR receives input from the healthcare worker, wherein the input is indicative of precursor data for an electronic prescription for the medication. The server EHR may use the precursor data in connection with constructing the electronic prescription. For instance, the precursor data may include an identifier for the patient, an identifier for the healthcare worker, an identifier for medication, a dosage amount of the medication, an identifier for the EHR, an indication as to how often the patient is to consume the medication, and a number of refills that are to be included in the electronic prescription. It is contemplated that the electronic prescription is to include at least one refill. Notably, the precursor data may fail to include an identifier for a pharmacy that is to fill the electronic prescription.

The client EHR then transmits the precursor data to the server EHR executing on a first server computing device that is in network communication with the client computing device. The server EHR may then transmit the precursor data to the server patient portal application executing on a second server computing device that is in network communication with the first server computing device. The server patient portal application then stores the precursor data in a data store accessible to the server patient portal application.

When the precursor data fails to include an identifier for a pharmacy that is to fill the electronic prescription, the server EHR can transmit a request for the identifier for the pharmacy to the server patient portal application. The server patient portal application may then forward the request to the client patient portal application executing on a patient computing device (e.g., a mobile computing device) operated by the patient that is in network communication with the second server computing device.

Subsequent to receiving the request, the client patient portal application may present the request in a graphical user interface (GUI) for the client patient portal application, wherein the GUI is displayed on a display of the patient computing device. The patient may then review the request, and the client patient portal application can receive (via the GUI) a selection of an identifier for a first pharmacy that is to receive the electronic prescription for the medication. Responsive to receiving the selection of the identifier for the first pharmacy, the client patient portal application transmits the identifier for the first pharmacy to the server patient portal application, wherein the server patient portal application can store the identifier for the first pharmacy in the data store in association with the precursor data.

The server EHR and the server patient portal application may cause the construction of the electronic prescription including at least one refill in several ways. In a first embodiment, the server EHR may construct an electronic prescription including the number of refills indicated by the precursor data. In a second embodiment, the server EHR constructs sub-prescriptions for the electronic prescription as the server EHR receives indications (from a pharmacy device or the server patient portal application) that the patient requires a refill of the electronic prescription. In the second embodiment, each sub-prescription is for the medication indicated by the precursor data and each sub-prescription includes a number of refills that is less than the number of refills indicated by the precursor data; however, the server EHR is configured to (over time) construct a number of sub-prescriptions having a (total) number of initial fills and refills equal to the number of refills indicated by the precursor data.

In the first embodiment, the server patient portal application transmits the precursor data and the identifier for the first pharmacy to the server EHR. Responsive to receiving the precursor data and the identifier for the first pharmacy, the server EHR constructs an electronic prescription for the patient based upon the precursor data and the identifier for the first pharmacy. The electronic prescription includes the number of refills specified in the precursor data. The server EHR also stores a copy of the electronic prescription in a data store accessible to the server EHR. Furthermore, the server EHR may also cause an identifier for the electronic prescription to be stored in association with the precursor data retained in the data store accessible to the server patient portal application. The server EHR then causes the electronic prescription to be received by a first pharmacy device of the first pharmacy, whereupon a pharmacist at the first pharmacy can fill the prescription.

In the second embodiment, prior to transmitting the precursor data and the identifier for the first pharmacy to the server EHR, the server patient portal application records (as part of the precursor data) that a sub-prescription fill has been initiated. The server EHR constructs a first sub-prescription for the electronic prescription based upon the precursor data and the identifier for the first pharmacy such that the first sub-prescription includes the precursor data (or a portion thereof) and the identifier for the first pharmacy. The first sub-prescription includes a number of refills less than the number of refills indicated by the precursor data. For instance, the first sub-prescription may include zero refills. However, as noted above, as the patient requires refills of the medication over time, the server EHR may construct additional sub-prescriptions such that initial fills and refills on the sub-prescriptions that are to be constructed is equal to the number of refills indicated by the precursor data. The server EHR also stores a copy of the first sub-prescription for the electronic prescription in the data store. Furthermore, the server EHR may also cause an identifier for the electronic prescription (and hence, the sub-prescription) to be stored in association with the precursor data retained in the data store accessible to the server patient portal application. Responsive to constructing the first sub-prescription, the server EHR causes the first sub-prescription to be received by the first pharmacy device of the first pharmacy, whereupon the pharmacist at the first pharmacy can fill the first sub-prescription.

Sometime thereafter, it is contemplated that the patient wishes to use a second pharmacy to fill remaining refills on the electronic prescription. As such, the client patient portal application may receive input indicative of the identifier for the electronic prescription and an identifier for the second pharmacy from the patient. The client patient portal application then transmits the identifier for the electronic prescription and the identifier for the second pharmacy to the server patient portal application, whereupon the server patient portal application stores the identifier for the second pharmacy in association with the precursor data.

In the first embodiment, the server patient portal application then transmits the identifier for the electronic prescription and the identifier for the second pharmacy to the server EHR. Responsive to receiving the identifier for the electronic prescription and the identifier for the second pharmacy, the server EHR identifies the electronic prescription based upon the identifier for the electronic prescription. The server ERH may then determine a number of refills remaining on the electronic prescription. Responsive to determining the number of refills remaining on the electronic prescription, the server EHR constructs a second electronic prescription based upon the electronic prescription and the identifier for the second pharmacy. The second electronic prescription includes the number of refills remaining on the electronic prescription. Responsive to constructing the second electronic prescription, the server EHR causes the second electronic prescription to be received by a second pharmacy device of the second pharmacy, whereupon a pharmacist at the second pharmacy can fill the prescription. The server EHR can also transmit messages to the first pharmacy device and the server patient portal application indicating that the first pharmacy is to cease providing further refills on the electronic prescription. Additionally, the server EHR can receive confirmation messages from the first pharmacy device and/or the server patient portal application indicating that the first pharmacy device and/or the server patient portal application acknowledge that the first pharmacy will cease providing refills for the electronic prescription.

In the second embodiment, responsive to receiving the identifier for the electronic prescription and the identifier for the second pharmacy from the client patient portal application, the server patient portal application verifies that constructing a second sub-prescription for the electronic prescription will not cause a total number of initial fills and refills on the sub-prescriptions that have been constructed for the electronic prescription to exceed the number of refills indicated by the precursor data.

In the second embodiment, the server patient portal application may then transmit the precursor data and the identifier for the second pharmacy to the server EHR. The server EHR then constructs a second sub-prescription based upon the precursor data and the identifier for the second pharmacy such that the second sub-prescription includes the precursor data (or a portion thereof) and the identifier for the second pharmacy. In an example, the second sub-prescription includes zero refills. Responsive to constructing the second sub-prescription, the server EHR causes the second sub-prescription to be received by the second pharmacy device of the second pharmacy. The server EHR also stores a copy of the second sub-prescription in the data store. The second pharmacy device may then present the second sub-prescription to a pharmacist at the second pharmacy, and the pharmacist can fill the second sub-prescription.

The above-described technologies present various advantages over conventional electronic prescription technologies. First, the above-described technologies save client computing resources as refills on an existing electronic prescription can be rerouted from a first pharmacy to a second pharmacy without the client EHR receiving manual input from the healthcare worker. Second, the above-described technologies are compatible with existing EHR architectures and thus do not require EHR retooling in order to function.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
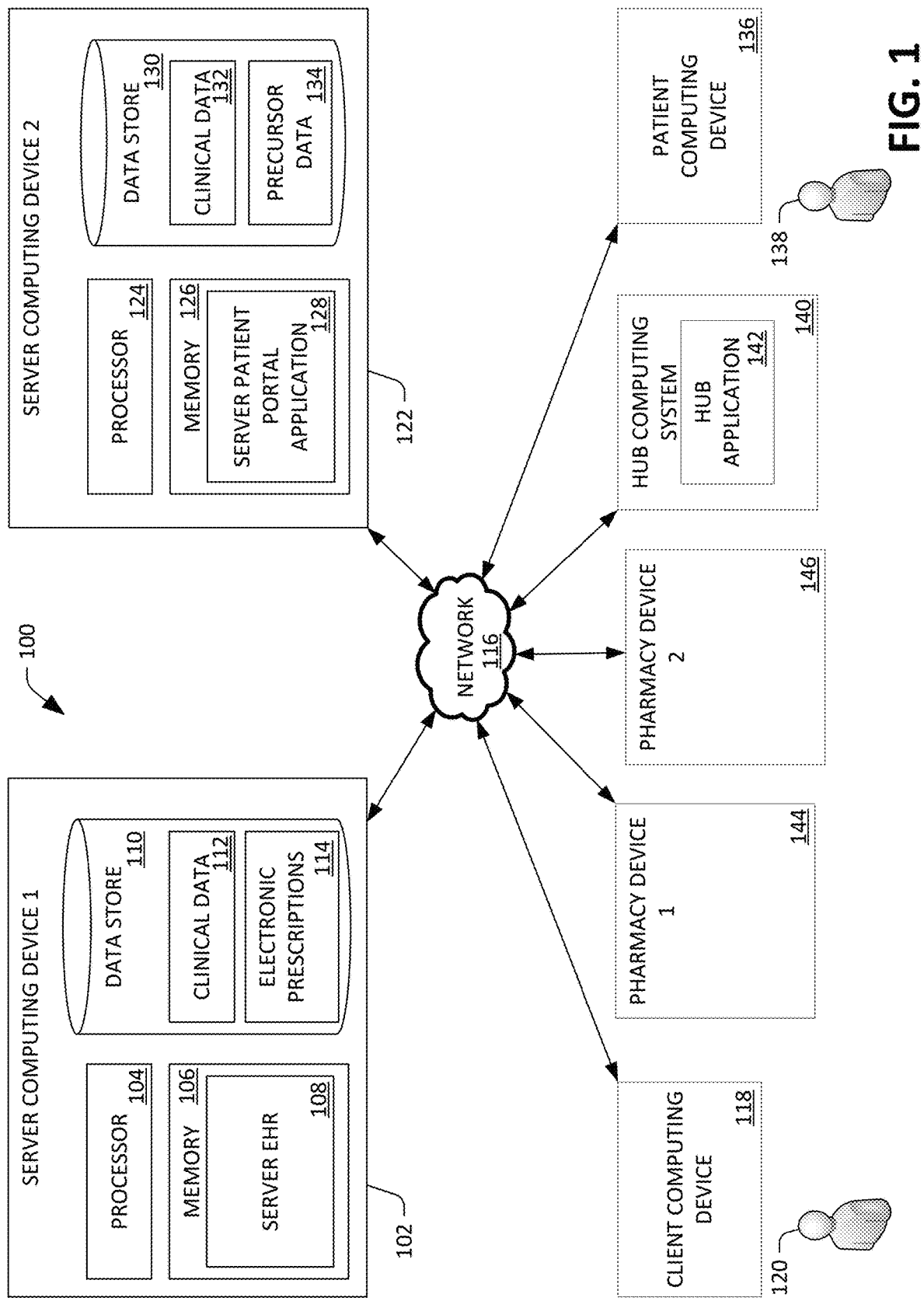
FIG. 1 is a functional block diagram of an exemplary computing system that facilitates redirecting refills on an electronic prescription.

Various technologies pertaining to redirecting refills on an electronic prescription are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

With reference to FIG. 1, an exemplary computing system 100 that facilitates redirecting refills on an electronic prescription is illustrated. The computing system 100 includes a first server computing device 102. The first server computing device 102 comprises a processor 104 and memory 106, wherein the memory 106 has a server electronic health records application (server EHR) 108 loaded therein. The server EHR 108 is generally configured to perform a variety of tasks related to patient healthcare in a healthcare facility (e.g., patient intake, prescription generation, patient record creation and maintenance, etc.). The first server computing device 102 also includes a data store 110 that comprises clinical data 112 (amongst other data) about patients, wherein the clinical data 112 is maintained by the server EHR 108. The clinical data 112 can include electronic health records, prescription records, claims data, patient/disease registries data, health surveys data, and/or clinical trials data. The data store 110 may additionally comprise electronic prescriptions 114 for patients.

Figure 2:
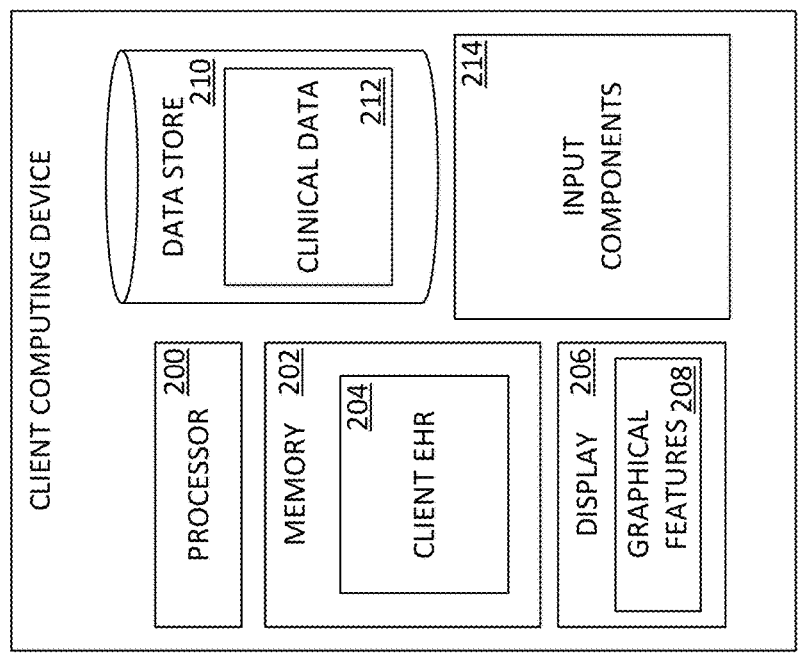
FIG. 2 is a functional block diagram of an exemplary client computing device.

The computing system 100 also includes a client computing device 118 operated by a healthcare worker 120. In an embodiment, the client computing device 118 can be a mobile computing device, such as a tablet computing device or smartphone. The client computing device 118 is in communication with the first server computing device 102 by way of a network 116 (e.g., the Internet, intranet). Turning briefly now to FIG. 2, the client computing device 118 includes a processor 200 and memory 202, wherein the memory 202 has a client electronic health records application (client EHR) 204 loaded therein. In general, the client EHR 204 is configured to interface with the server EHR 108 executing on the first server computing device 102, thereby providing the healthcare worker 120 with access to functionality of the server EHR 108.

The client computing device 118 may also include a data store 210 comprising clinical data 212 about patients. It is understood that there may be some overlap between the clinical data 212 stored in the data store 210 and the clinical data 112 stored in the data store 110. The client computing device 118 may include a display 206, wherein graphical features 208 may be presented thereon. Furthermore, the client computing device 118 may include input components 214 (e.g., mouse, keyboard, touchscreen, microphone, etc.) suitable for data input.

Turning back to FIG. 1, the computing system 100 includes a second server computing device 122 that may be in communication with the first server computing device 102 by way of the network 116. In an embodiment, the second server computing device 122 may be in communication with the first server computing device 102 by of another network (i.e., not the network 116). The second server computing device 122 comprises a processor 124 and memory 126, wherein the memory 126 has a server patient portal application 128 loaded therein. The server patient portal application 128 is configured to allow a patient 138 to access his or her health data, including prescription medications, health records, communication with healthcare providers, input self-reported patient health data, etc. The patient 138 may interface with the server patient portal application 128 by way of a patient computing device 136 (described below).

The second server computing device 122 may include a data store 130. The data store 130 may comprise clinical data 132 for patients, wherein the clinical data 132 is a subset of the clinical data 112 maintained by the server EHR 108. Thus, the server EHR 108 is configured to provide the server patient portal application 128 with the clinical data 112, wherein an administrator (not shown) of the server EHR 108 can set forth policies as to what data is included in the clinical data 132 (and the format of such data). In addition, the server patient portal application 128 can maintain data provided directly by the patient 138 to the server patient portal application 128. The data store 130 may also include precursor data 134 for electronic prescriptions for patients (described below).

Figure 3:
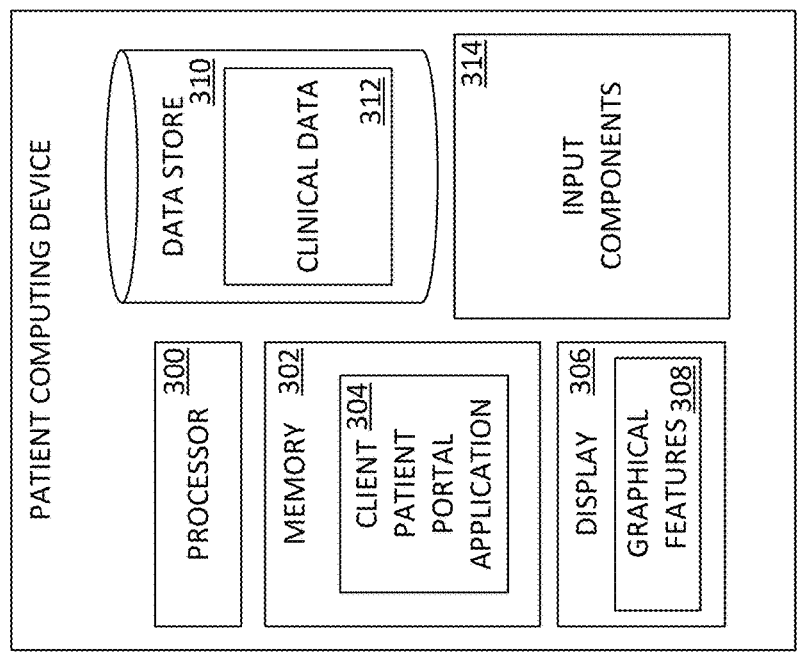
FIG. 3 is a functional block diagram of an exemplary patient computing device.

The computing system 100 additionally includes a patient computing device 136 operated by the patient 138. In an embodiment, the patient computing device 136 can be a mobile computing device, such as a tablet computing device, a wearable computing device (e.g., a smartwatch), or a smartphone. The patient computing device 136 may also be a desktop computing device or a laptop computing device. The patient computing device 136 is in communication with the second server computing device 122 by way of the network 116 (or another network). Referring briefly now to FIG. 3, the patient computing device 136 includes a processor 300 and memory 302, wherein the memory 302 has a client patient portal application 304 loaded therein. In general, the client patient portal application 304 is configured to interface with the server patient portal application 128 to allow the patient 138 to access his or her health data that is maintained by the server patient portal application 128.

The patient computing device 136 may also include a data store 310 comprising clinical data 312 (as well as other data) about the patient 138. The patient computing device 136 may include a display 306, wherein graphical features 308 may be presented thereon. Furthermore, the patient computing device 136 may include input components 314 (e.g., mouse, keyboard, touchscreen, microphone, etc.) suitable for data input.

The computing system 100 includes a first pharmacy device 144 of a first pharmacy and a second pharmacy device 146 of a second pharmacy. In an embodiment, the first pharmacy device 144 and/or the second pharmacy device 146 may be computing devices. In another embodiment, the first pharmacy device 144 and/or the second pharmacy device 146 may be fax machines.

The computing system 100 may additionally include a hub computing system 140. The hub computing system 140 comprises a processor (not shown) and memory (not shown), wherein the memory has a hub application 142 loaded therein. The hub computing system 140 may be referred to as a transaction hub and may be in communication with the first server computing device 102, the first pharmacy device 144, and the second pharmacy device 146. In general, the hub application 142 is configured to route an electronic prescription transmitted from the server EHR 108 to a pharmacy device. For instance, the hub computing system 140 may maintain a master list of pharmacies, and the hub application 142 may route an electronic prescription to the pharmacy identified in the electronic prescription using the master list of pharmacies. Additionally, the hub application 142 may be configured to verify that an electronic prescription has not been tampered with using an electronic signature in the electronic prescription.

Exemplary operation of the computing system 100 is now set forth. It is contemplated that the healthcare worker 120 has had a patient encounter with the patient 138 and that the healthcare worker 120 has decided to prescribe a medication to the patient 138. Furthermore, it is contemplated that an electronic prescription for the medication is to include at least one refill. The client computing device 118 can receive user credentials from the healthcare worker 120 and can transmit the user credentials to the first server computing device 102. The server EHR 108 can authenticate the healthcare worker 120 based upon the user credentials, and can provide the healthcare worker 120 with access to the functionality of the server EHR 108 via the client EHR 204 executing on the client computing device 118.

The client EHR 204 may then receive precursor data as input from the healthcare worker 120. The precursor data is data that the server EHR 108 is to use to construct an electronic prescription. For instance, the precursor data may include an identifier for the patient 138, an identifier for the healthcare worker 120, an identifier for the medication that is to be prescribed, a dosage amount of the medication, an identifier for the server EHR 108, an indication as to how often the patient is to consume the medication, and a number of refills that are to be included in the electronic prescription. The precursor data may also include an electronic signature for a healthcare worker 120. Notably, the precursor data may fail to include an identifier for a pharmacy that is to fill the electronic prescription. The client EHR 204 may then transmit the precursor data to the server EHR 108.

Responsive to receiving the precursor data, the server EHR 108 transmits the precursor data to the server patient portal application 128. The server patient portal application 128 then stores the precursor data in the data store 130 as the precursor data 134. It is to be appreciated that the server EHR 108 may or may not retain the precursor data for the electronic prescription in the data store 110. However, it is also to be appreciated that the server patient portal application 128 may retain the precursor data in the data store 130 indefinitely.

In the event that the precursor data fails to include an identifier for a pharmacy that is to fill the electronic prescription, the server EHR 108 may generate and transmit a request for an identifier for a pharmacy to the server patient portal application 128. The request may include an identifier for the medication that is to be prescribed and an identifier for the patient 138. The server patient portal application 128 may then forward the request to the client patient portal application 304 executing on the patient computing device 136 based upon the identifier for the patient 138 in the request. Alternatively, the server patient portal application 128 may generate the request and transmit the request directly to the client patient portal application 304 based upon the identifier for the patient 138.

The client patient portal application 304 can then present the request to the patient 134. For instance, the client patient portal application 304 can present the request on the display 306. The client patient portal application 304 may then receive an identifier for a first pharmacy that is to provide the medication as input from the patient 138. The client patient portal application 304 can then transmit the identifier for the first pharmacy to the server patient portal application 128, wherein the server patient portal application 128 stores the identifier for the first pharmacy in association with the precursor data 134 in the data store 130.

In an embodiment, the server patient portal application 128 maintains a list of identifiers for pharmacies that have attributes that are desirable by the patient 138 (e.g., located in an area near a residence of the patient 138, low prices for medications, high customer ratings, etc.) In the embodiment, the server patient portal application 128 transmits identifiers for pharmacies in the list to the client patient portal application 304 along with the request for the identifier for the pharmacy. The client patient portal application 304 can then present the identifiers within a GUI presented on the display 306. The GUI can then receive a selection of an identifier for a first pharmacy in the identifiers from the patient 138. The client patient portal application 304 can then transmit the identifier for the first pharmacy to the server patient portal application 128, wherein the server patient portal application 128 can store the identifier for the first pharmacy in association with the precursor data 134 in the data store 130.

The server patient portal application 128 may then transmit the precursor data 134 and the identifier for the first pharmacy to the server EHR 108. The server EHR 108 and the server patient portal application 128 may cause the construction of an electronic prescription including at least one refill in several ways. In a first embodiment, the server EHR 108 may construct an electronic prescription including the number of refills indicated by the precursor data. In a second embodiment, the server EHR 108 constructs sub-prescriptions for the electronic prescription as the server EHR 108 receives indications that refills are required by the patient 138. In the second embodiment, each sub-prescription includes a number of refills less than the number of refills indicated by the precursor data (e.g., zero refills); however, the server EHR 108 is configured to (over time) construct a number of sub-prescriptions having a combined number of fills and refills equal to the number of refills indicated by the precursor data.

In the first embodiment, the server EHR 108 constructs an electronic prescription based upon the precursor data and the identifier for the first pharmacy such that the electronic prescription includes the precursor data (or a portion thereof) and the identifier for the first pharmacy. The electronic prescription includes the number of refills indicated by the precursor data. In an example, the electronic prescription may include twelve refills. Responsive to constructing the electronic prescription, the server EHR 108 transmits the electronic prescription to the hub application 142 executing on the hub computing system 140. The server EHR 108 also stores a copy of the electronic prescription in the data store 110. Furthermore, the server EHR 108 may also cause an identifier for the electronic prescription to be stored in association with the precursor data 134 of the data store 130. The hub application 142 may then route the electronic prescription, by way of the network 116, to the first pharmacy device 144 of the first pharmacy identified in the electronic prescription. The first pharmacy device 144 may then present the electronic prescription to a pharmacist at the first pharmacy, and the pharmacist can fill the prescription.

In the second embodiment, prior to transmitting the precursor data and the identifier for the first pharmacy to the server EHR 108, the server patient portal application 128 records (in the precursor data 134) that a sub-prescription for the electronic prescription has been initiated. The server EHR 108 constructs a first sub-prescription based upon the precursor data (or a portion thereof) and the identifier for the first pharmacy such that the first sub-prescription includes the precursor data (or a portion thereof) and the identifier for the first pharmacy. In an example, the first sub-prescription may include zero refills (i.e., the first sub-prescription includes only an initial fill). However, as noted above, as the patient 138 requires refills of the medication over time, the server EHR 108 may construct additional sub-prescriptions such that a total number of fills and refills on the sub-prescriptions constructed is equal to the number of refills (in addition to an initial fill) indicated by the precursor data. In an example, the precursor data may indicate that the electronic prescription is to include an initial fill and eleven refills, and hence the server EHR 108 may (over time) construct twelve sub-prescriptions, each sub-prescription including an initial fill and zero refills. In another example, the server EHR 108 may (over time) construct four sub-prescriptions, each sub-prescription including an initial fill and two refills.

In the second embodiment, responsive to constructing the first sub-prescription, the server EHR 108 transmits the first sub-prescription to the hub application 142 executing on the hub computing system 140. The server EHR 108 also stores a copy of the first sub-prescription in the data store 110. Furthermore, the server EHR 108 may also cause an identifier for the electronic prescription (and hence, the first sub-prescription) to be stored in association with the precursor data 134 of the data store 130. The hub application 142 may then route the first sub-prescription, by way of the network 116, to the first pharmacy device 144 for the first pharmacy identified in the first sub-prescription. The first pharmacy device 144 may then present the first sub-prescription for the electronic prescription to a pharmacist at the first pharmacy, and the pharmacist can fill the first sub-prescription.

Subsequently, it is contemplated that the patient 138 wishes to change the pharmacy that fills the electronic prescription from the first pharmacy to a second pharmacy. For instance, when the electronic prescription includes twelve refills, the electronic prescription may have been filled by the first pharmacy four times, and the patient may wish for remaining refills on the electronic prescription to be filled by the second pharmacy. As such, the client patient portal application 304 may receive input indicative of the (existing) electronic prescription and an identifier for a second pharmacy from the patient. The client patient portal application 304 then transmits an identifier for the electronic prescription and the identifier for the second pharmacy to the server patient portal application 128, whereupon the server patient portal application 128 stores the identifier for the second pharmacy in association with the precursor data 134.

In embodiment where the server patient portal application 128 maintains a list of identifiers for pharmacies that have attributes that are desirable by the patient 138 (described above), the client patient portal application 304 can transmit a request to the server patient portal application 128 thereby causing the list and identifiers for existing electronic prescriptions of the patient 138 to be presented within the GUI presented on the display 306. The GUI can then receive a selection of an identifier for the second pharmacy in the identifiers from the patient 138 and a selection of the identifier for the (existing) electronic prescription, thereby causing the server patient portal application 128 to receive the identifier for the electronic prescription and the identifier for the second pharmacy.

In the first embodiment, the server patient portal application 128 then transmits the identifier the electronic prescription and the identifier for the second pharmacy to the server EHR 108. Responsive to receiving the identifier for the electronic prescription and the identifier for the second pharmacy, the server EHR 108 identifies the electronic prescription based upon the identifier for the electronic prescription. More specifically, the server EHR 108 may execute a search over the electronic prescriptions 114 retained in the data store 110, wherein the search is based upon the identifier for the electronic prescription. The search yields search results, wherein the search results are indicative of the electronic prescription. The server ERH 108 may then determine a number of refills remaining on the electronic prescription. Determining the number of refills may involve communicating with the server patient portal application 128 and/or the first pharmacy device 144. Responsive to determining the number of refills remaining on the electronic prescription, the server EHR 108 constructs a second electronic prescription based upon the electronic prescription and the identifier for the second pharmacy such that the second electronic prescription includes the precursor data (or a portion thereof) and the identifier for the second pharmacy. The second electronic prescription includes the number of refills remaining on the (original) electronic prescription.

In the first embodiment, responsive to constructing the second electronic prescription, the server EHR 108 may transmit the second electronic prescription to the hub application 142 executing on the hub computing system 140. The server EHR 108 also stores a copy of the second electronic prescription in the data store 110. The hub application 142 may then route the second electronic prescription to the second pharmacy device 146 of the second pharmacy identified in the second electronic prescription. The second pharmacy device 146 may then present the electronic prescription to a pharmacist at the second pharmacy, and the pharmacist can fill the prescription.

In the first embodiment, prior to transmitting the second electronic prescription to the second pharmacy device, the server EHR 108 may transmit a first message to the first pharmacy device 144 (by way of the hub computing system 140). The first message indicates that the first pharmacy is to cease further refilling of the electronic prescription. The first pharmacy device 144 may then transmit a second message to the server EHR 108 (by way of the hub computing system 140). The second message indicates that the first pharmacy will cease refilling the electronic prescription. Responsive to receiving the second message, the server EHR 108 may transmit the second message (or another message derived therefrom) to the server patient portal application 128.

In the second embodiment, responsive to receiving the identifier for the electronic prescription and the identifier for the second pharmacy from the client patient portal application 304, the server patient portal application 128 verifies that constructing a second sub-prescription (or another sub-prescription) will not cause the total number of fills and refills for sub-prescriptions that have been constructed for the electronic prescription to exceed the number of refills indicated by the precursor data. For instance, the server patient portal application 128 may retrieve the precursor data by executing a search over the data store 130 based on the identifier for the electronic prescription. The search yields search results, wherein the search results are indicative of the electronic prescription (and hence, the sub-prescriptions of the electronic prescription). The server patient portal application 128 can verify that constructing the second sub-prescription will not cause the total number of fills and refills for sub-prescriptions that have been constructed for the electronic prescription to exceed the number of refills indicated by the precursor data.

In the second embodiment, the server patient portal application 128 may then transmit the precursor data (or a portion thereof) and the identifier for the second pharmacy to the server EHR 108. The server EHR 108 then constructs a second sub-prescription based upon the precursor data (or a portion thereof) and the identifier for the second pharmacy such that the second sub-prescription includes the precursor data (or a portion thereof) and the identifier for the second pharmacy. In an example, the second sub-prescription may include zero refills (and hence only an initial fill). Responsive to constructing the second sub-prescription, the server EHR 108 transmits the second sub-prescription to the hub application 142 executing on the hub computing system 140. The server EHR 108 also stores a copy of the second sub-prescription in the data store 110. The hub application 142 may then route the second sub-prescription, by way of the network 116, to the second pharmacy device 146 for the second pharmacy identified in the second sub-prescription. The second pharmacy device 146 may then present the second sub-prescription to a pharmacist at the second pharmacy, and the pharmacist can fill the second sub-prescription.

In an embodiment, subsequent to transmitting an electronic prescription (or a sub-prescription) to the hub application 142, the server EHR 108 may transmit a notification to the server patient portal application 128 indicating that the server EHR 108 has transmitted the electronic prescription (or the sub-prescription) to a pharmacy device (by way of the hub computing system 140). The server patient portal application 128 may then forward the notification to the patient computing device 136, wherein the patient computing device 136 can present the notification to the patient 138 on the display 306 of the patient computing device 136.

In an embodiment, the above-described functionality may comply with National Council for Prescription Drug Programs (NCPDP) standards.

In an embodiment, the above-described functionality may accommodate refills including variable dosage patterns such as tapering or loading regimens.

In an embodiment, the above-described functionality may be used to subdivide a refill on an existing electronic prescription. For example, in the case of a monthly prescription, the EHR and patient portal application described above may "split" the monthly prescription into four week-long prescriptions and direct each week-long prescription to a different pharmacy.

While the above-described functionality has been described as being primarily performed using the server EHR 108, other possibilities are contemplated. In an embodiment, the above-described functionality may be accomplished through use of a prescription module that can be incorporated into an EHR. In another embodiment, the above-described functionality may be primarily accomplished through use of a prescription application that executes on a computing device that is in communication with the first server computing device 102 by way of the network 116. In yet another embodiment, the server EHR 108 and the server patient portal application 128 may execute on the same server computing device.

In an embodiment, the server EHR 108 may be configured to perform some or all of the functionality described above as being performed by the server patient portal application 128 such that the above-described functionality may be performed using existing components of the server EHR 108.

While the above-described process has been described as including a single change of pharmacies, it is to be understood that the above-described technologies may be used to change the pharmacy that fills an electronic prescription many times.

FIGS. 4-7 illustrate exemplary methodologies relating to redirecting refills of an existing electronic prescription from a first pharmacy to a second pharmacy specified by a patient. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Figure 4:
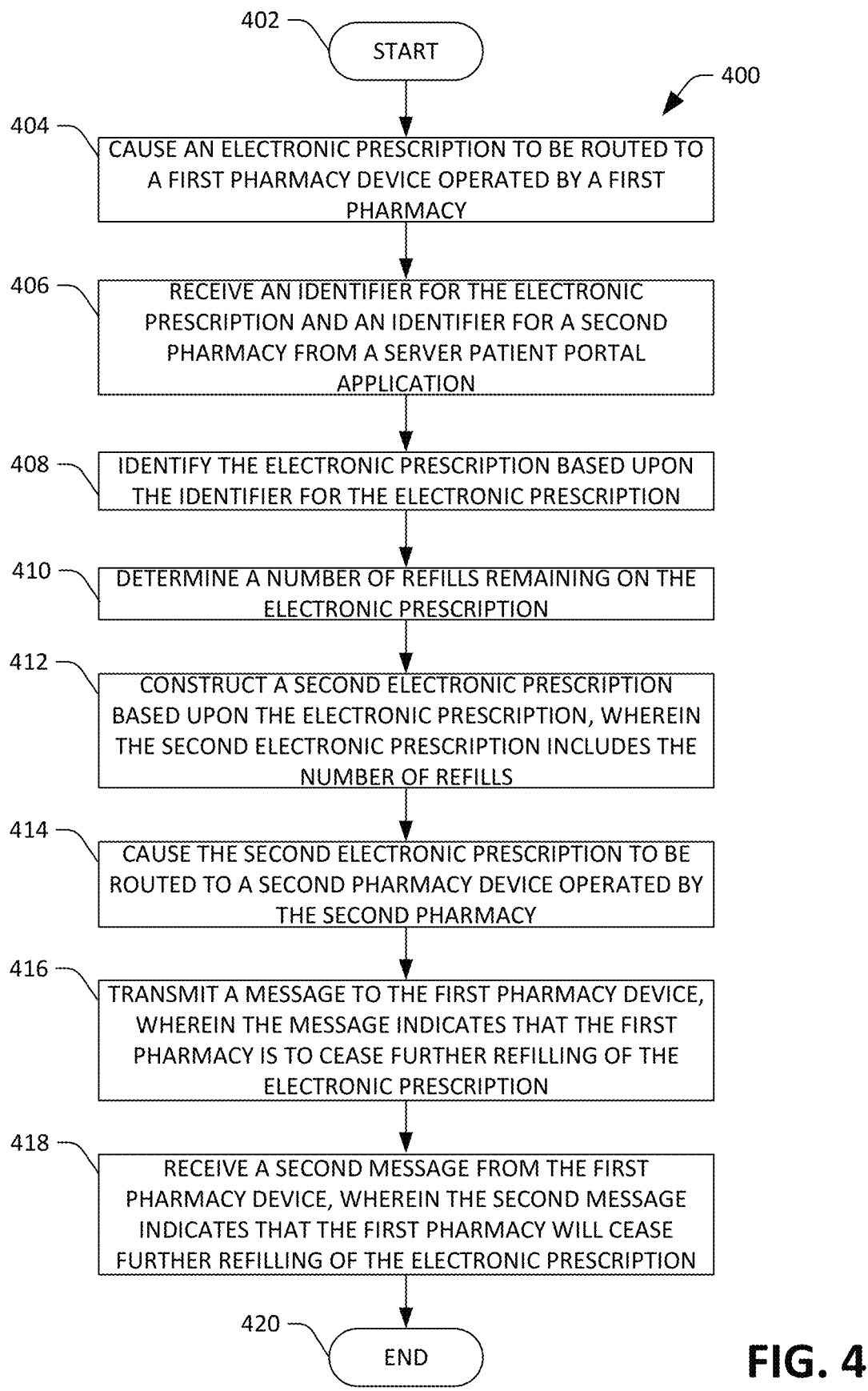
FIG. 4 is a flow diagram illustrating an exemplary methodology executed by a server electronic health records application (server EHR) for redirecting refills on an electronic prescription.

Turning now to FIG. 4, a methodology 400 performed by a server EHR executing on a server computing device that facilitates redirecting refills on an existing electronic prescription is illustrated. The methodology 400 begins at 402, and at 404, responsive to constructing an electronic prescription for a patient, the server EHR causes the electronic prescription to be routed to a first pharmacy device of a first pharmacy. The electronic prescription includes at least one refill.

Subsequently, at 406, the server EHR receives an identifier for the electronic prescription and an identifier for a second pharmacy from a server patient portal application. At 408, responsive to receiving the identifier for the electronic prescription and the identifier for the second pharmacy from the server patient portal application, the server EHR identifies the electronic prescription based upon the identifier for the electronic prescription. At 410, responsive to identifying the electronic prescription, the server EHR determines a number of refills remaining on the electronic prescription. At 412, responsive to determining the number of refills, the server EHR constructs a second electronic prescription based upon the electronic prescription. The second electronic prescription includes the number of refills. At 414, the server EHR causes the second electronic prescription to be routed to a second pharmacy device of the second pharmacy based upon the identifier for the second pharmacy. At 416, the server EHR transmits a first message to the first pharmacy device. The first message indicates that the first pharmacy is to cease further refilling of the electronic prescription. At 418, the server EHR receives a second message from the first pharmacy device. The second message indicates that the first pharmacy will cease further refilling of the electronic prescription. The methodology 400 concludes at 420.

Figure 5:
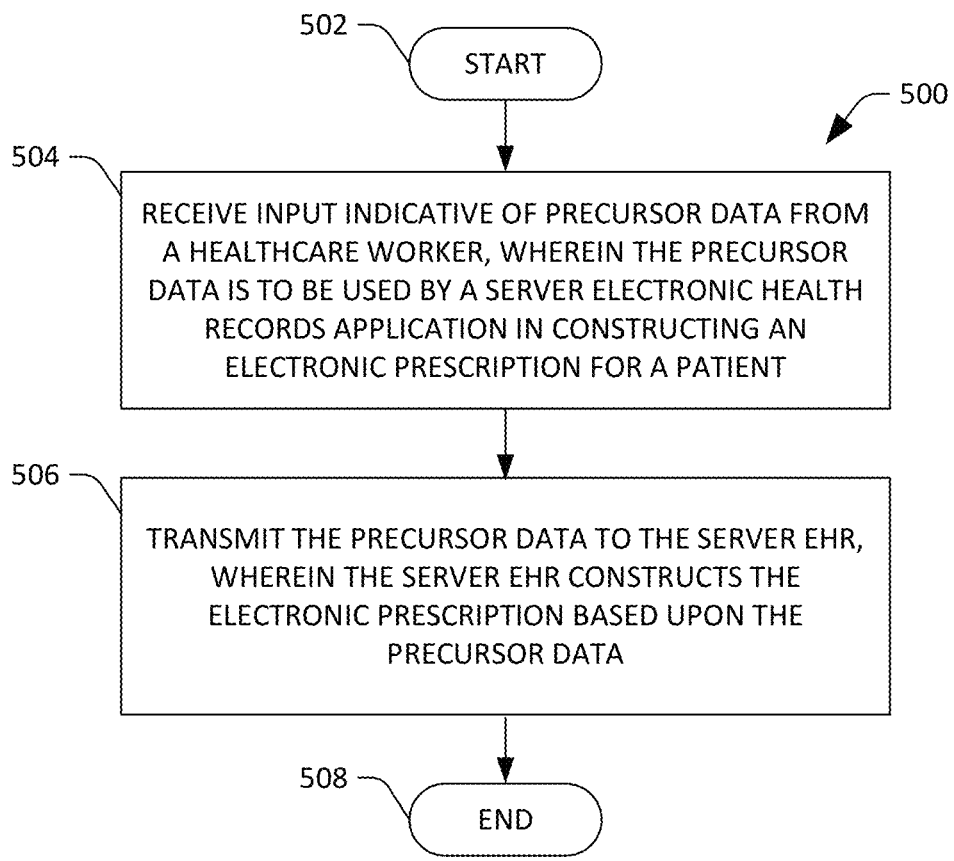
FIG. 5 is a flow diagram illustrating an exemplary methodology executed by a client electronic health records application (client EHR) for constructing an electronic prescription including refills.

Referring now to FIG. 5, a methodology 500 performed by a client EHR executing on a client computing device of a healthcare worker that facilitates constructing an electronic prescription is illustrated. The methodology 500 begins at 502, and at 504, the client EHR receives input indicative of precursor data from the healthcare worker. The precursor data is to be used by a server EHR in constructing the electronic prescription for the patient. At 506, the client EHR transmits the precursor data to the server EHR, whereupon the server EHR constructs the electronic prescription based upon the precursor data. The methodology 500 concludes at 508.

Figure 6:
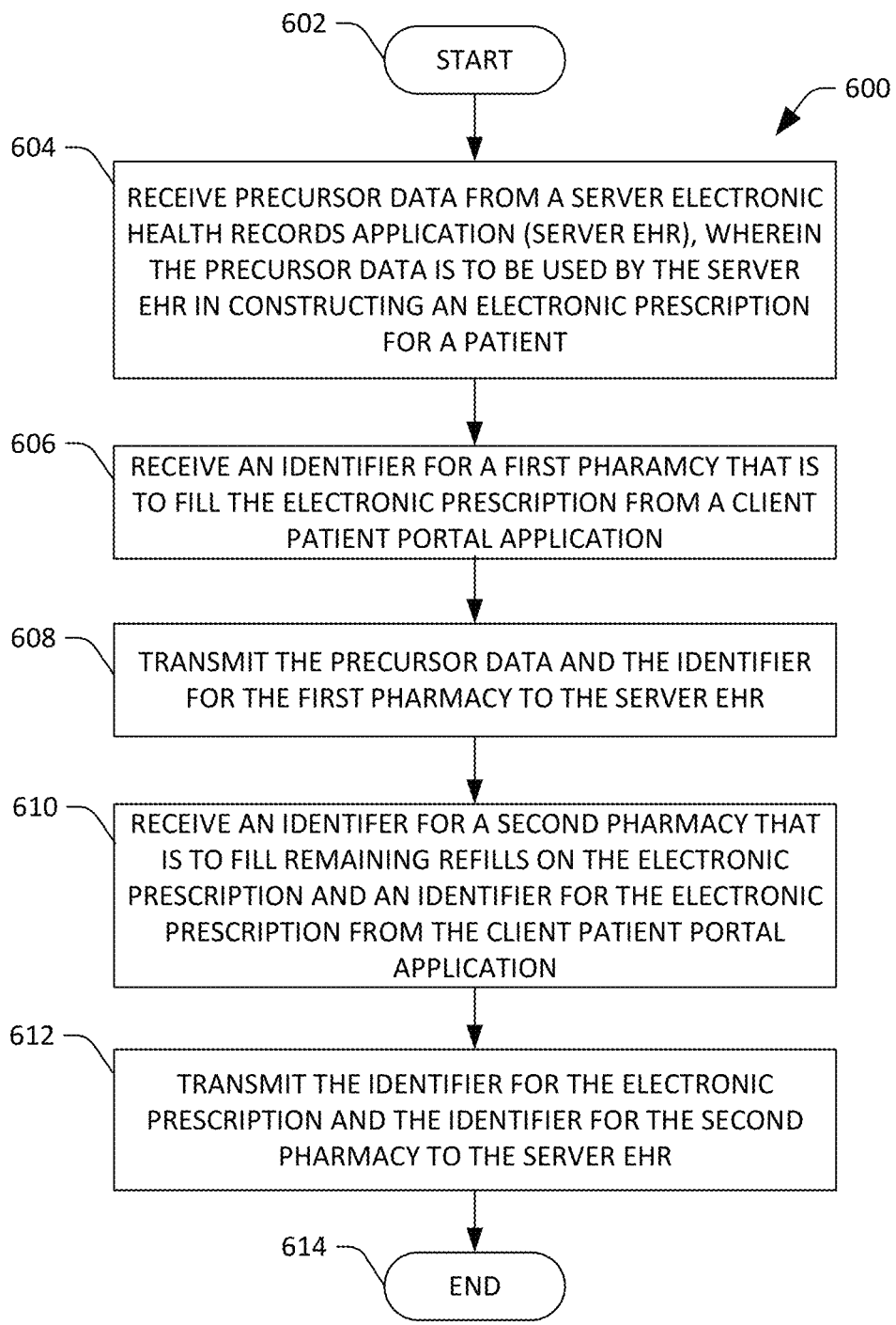
FIG. 6 is a flow diagram illustrating an exemplary methodology executed by a server patient portal application for redirecting refills on an electronic prescription.

Turning now to FIG. 6, a methodology 600 performed by a server patient portal application executing on a server computing device that facilitates redirecting refills on an existing electronic prescription is illustrated. The methodology 600 begins at 602, and at 604 the server patient portal application receives precursor data from a server EHR. The precursor data is to be used by the server EHR in constructing an electronic prescription for a patient. The precursor data indicates that the electronic prescription is to include at least one refill. At 606, the server patient portal application receives an identifier for a first pharmacy that is to fill the electronic prescription from a client patient portal application executing on a patient computing device. At 608, the server patient portal application transmits the precursor data and the identifier for the first pharmacy to the server EHR. The server EHR then constructs an electronic prescription based upon the precursor data and the identifier for the first pharmacy.

Subsequently, at 610, the server patient portal application receives an identifier for a second pharmacy that is to fill remaining refills on the electronic prescription and an identifier for the electronic prescription from the client patient portal application. At 612, the server patient portal application transmits the identifier for the second pharmacy and the identifier for the electronic prescription to the server EHR. The server EHR then constructs a second electronic prescription based upon the electronic prescription and the identifier for the second pharmacy, wherein the second electronic prescription includes a number of refills equal to the remaining refills on the electronic prescription. The methodology 600 concludes at 614.

Figure 7:
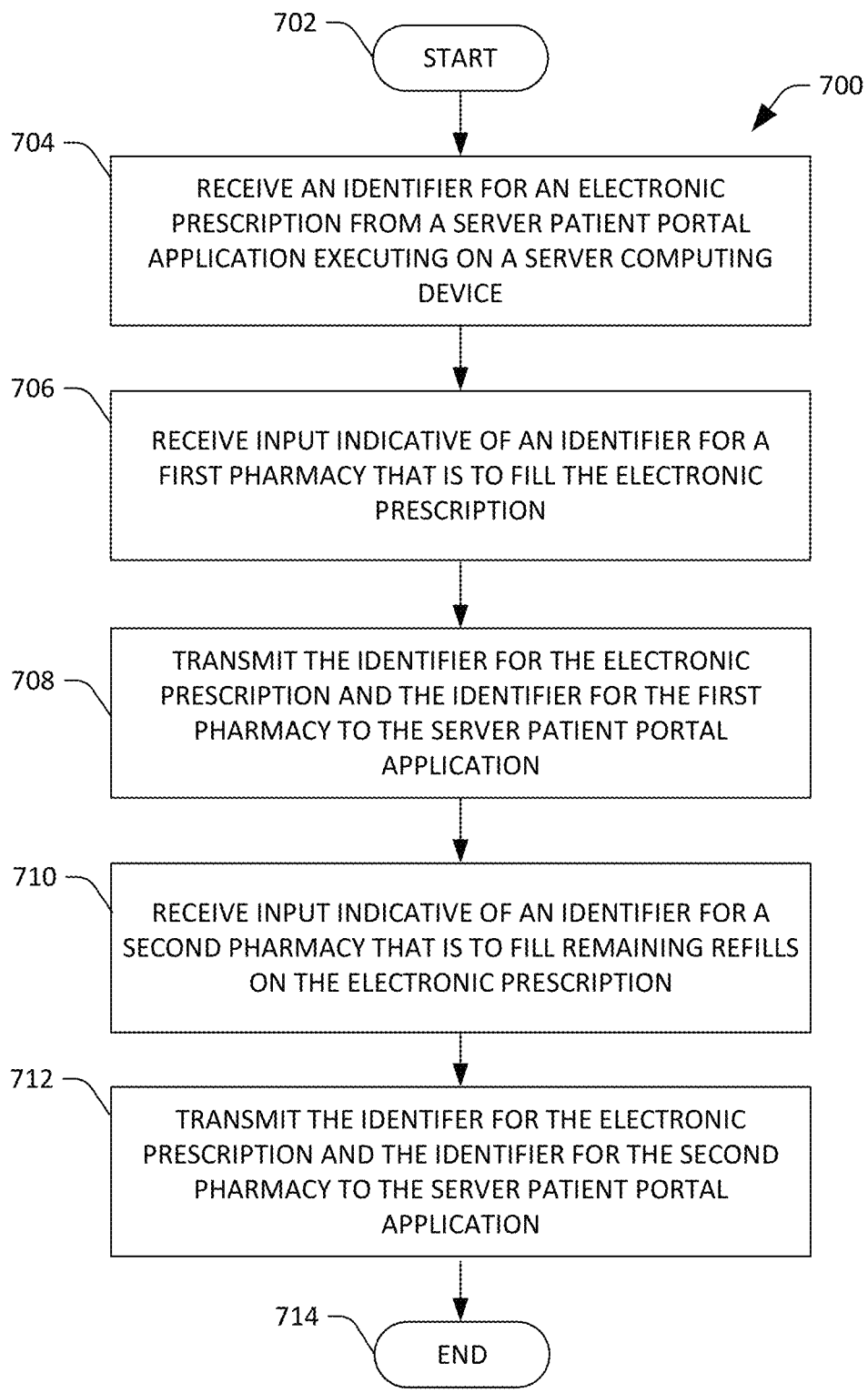
FIG. 7 is a flow diagram illustrating an exemplary methodology executed by a client patient portal application for redirecting refills on an electronic prescription.

With reference now to FIG. 7, a methodology 700 performed by a client patient portal application executing on a patient computing device of a patient that facilitates redirecting refills on an existing electronic prescription is illustrated. The methodology 700 begins at 702, and at 704 the client patient portal application receives an identifier for an electronic prescription for the patient that is to be constructed from a server patient portal application. The electronic prescription is to include at least one refill. At 706, the client patient portal application receives input from the patient indicative of an identifier for a first pharmacy that is to fill the electronic prescription. At 708, the client patient portal application transmits the identifier for the electronic prescription and the identifier for the first pharmacy to the server patient portal application.

Subsequently, at 710, the client patient portal application receives input indicative of an identifier for a second pharmacy that is to fill remaining refills on the electronic prescription. At 712, the client patient portal application transmits the identifier for the electronic prescription and the identifier for the second pharmacy to the server patient portal application. The methodology 700 concludes at 714.

Figure 8:
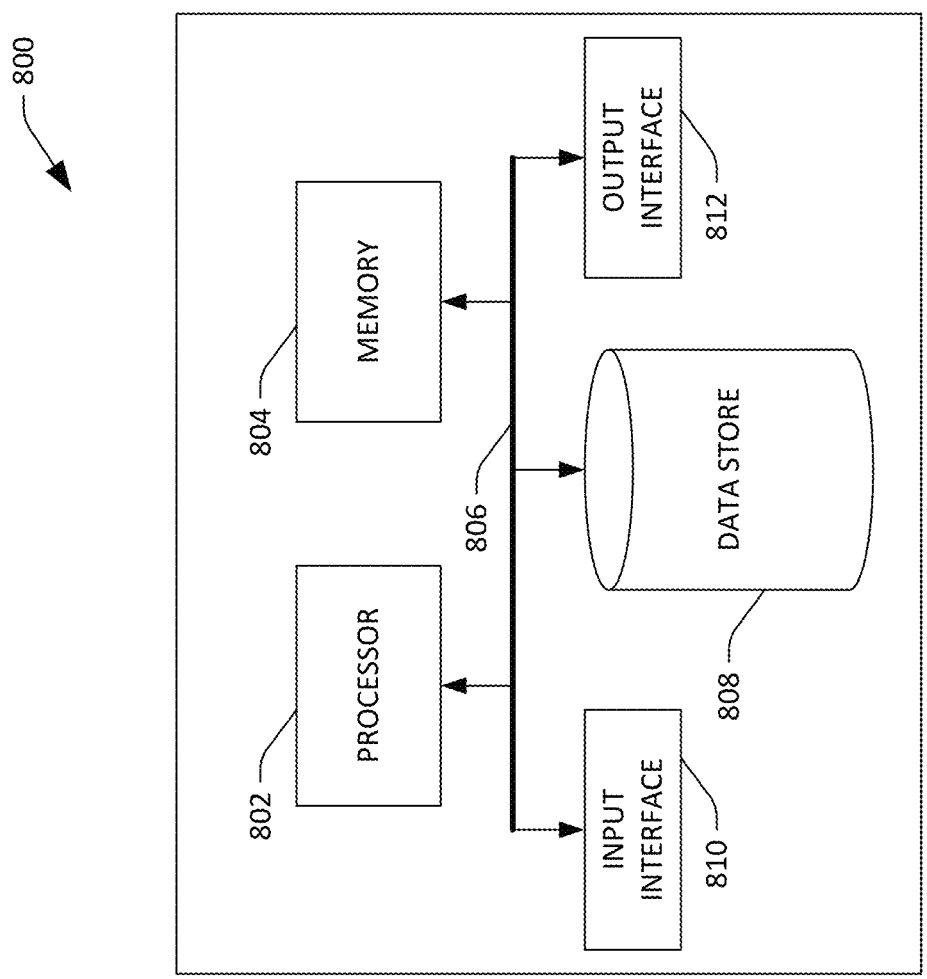
FIG. 8 is an exemplary computing system.

Referring now to FIG. 8, a high-level illustration of an exemplary computing device 800 that can be used in accordance with the systems and methodologies disclosed herein is illustrated. For instance, the computing device 800 may be used in a system that executes an EHR. By way of another example, the computing device 800 can be used in a system that executes a patient portal application. The computing device 800 includes at least one processor 802 that executes instructions that are stored in a memory 804. The instructions may be, for instance, instructions for implementing functionality described as being carried out by one or more components discussed above or instructions for implementing one or more of the methods described above. The processor 802 may access the memory 804 by way of a system bus 806. In addition to storing executable instructions, the memory 804 may also store clinical data, electronic prescriptions, precursor data, etc.

The computing device 800 additionally includes a data store 808 that is accessible by the processor 802 by way of the system bus 806. The data store 808 may include executable instructions, clinical data, electronic prescriptions, precursor data, etc. The computing device 800 also includes an input interface 810 that allows external devices to communicate with the computing device 800. For instance, the input interface 810 may be used to receive instructions from an external computer device, from a user, etc. The computing device 800 also includes an output interface 812 that interfaces the computing device 800 with one or more external devices. For example, the computing device 800 may display text, images, etc. by way of the output interface 812.

It is contemplated that the external devices that communicate with the computing device 800 via the input interface 810 and the output interface 812 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 800 in a manner free from constraints imposed by input devices such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 800 may be a distributed system. Thus, for instance, several devices may be in communication by way of a network connection and may collectively perform tasks described as being performed by the computing device 800.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A server computing device, comprising:
a processor; and
memory storing a server patient portal application, that, when executed by the processor, causes the processor to perform acts comprising:
transmitting precursor data for an electronic prescription for a medication for a patient to a server electronic health records application (server EHR) executing on a second server computing device, where the server FUR constructs the electronic prescription for the medication for the patient based upon the precursor data, where the precursor data comprises an identifier for a medication that is to be prescribed to the patient and an electronic signature for a healthcare worker who is prescribing the medication, and further where the server FUR causes the electronic prescription to be routed to a first pharmacy device of a first pharmacy, where the electronic prescription includes at least one refill, and further where the electronic prescription is filled by the first pharmacy;
receiving an identifier for the electronic prescription and an identifier for a second pharmacy from a client patient portal application executing on a patient computing device that is in communication with the server patient portal application by way of a network;
transmitting the identifier for the electronic prescription and the identifier tar the second pharmacy to the server EHR application, where the server EHR application:

executes a search over a computer-readable data store that comprises electronic prescriptions for a plurality of patients to identify the prescription;

determines a number of refills remaining on the electronic prescription responsive to identifying the electronic prescription;

in response to determining the number of refills remaining on the electronic prescription, constructs a second electronic prescription based upon the electronic prescription, where the second electronic prescription includes the number of refills;

constructs a second electronic prescription based upon the electronic prescription, wherein the second electronic prescription includes the number of refills;

causes a message to be received by the first pharmacy device, where the message indicates that the first pharmacy is to cease further refilling of the electronic prescription; and causes the second electronic prescription to be routed to a second pharmacy device of the second pharmacy based upon the identifier for the second pharmacy, where the second electronic prescription is filled by the second pharmacy.

2. The server computing device of claim 1, wherein the first pharmacy device is a first fax machine or a first computing system, and the second pharmacy device is a second fax machine or a second computing system.

3. The server computing device of claim 1, wherein the precursor data further comprises:
an identifier for the patient;
an identifier for the healthcare worker that is prescribing the electronic prescription;
a dosage amount of the medication for the patient;
an indication as to how often the patient is to consume the medication; and
an indication of a total number of refills that are to be included in the electronic prescription.

4. The server computing device of claim 1, wherein the precursor data fails to include an identifier for the first pharmacy.

5. The server computing device of claim 1, the acts further comprising transmitting identifiers for pharmacies to the client patient portal application, where the identifier for the second pharmacy is included in the identifier for the pharmacies, where the client patient portal application displays the identifiers for the pharmacies on a display of the patient computing device, and further where the client patient portal application transmits the identifier for the second pharmacy to the server patient portal application in response to receiving a selection of the identifier for the second pharmacy.

6. The server computing device of claim 1,
where, in connection with causing the second electronic prescription to be routed to the second pharmacy, the server EHR transmits the second electronic prescription to a hub application executing on a hub computing system, where the hub application routes the second electronic prescription to the second pharmacy device.

7. The server computing device of claim 1, wherein the first electronic prescription is constructed during a first month, wherein the second electronic prescription is constructed during a second month that occurs subsequent to the first month.

8. A method performed by a server patient portal application executing on a server computing device, the method comprising:

transmitting precursor data for an electronic prescription for a medication for a patient to a server electronic health records application (server EHR) executing on a second server computing device, where the server EHR constructs the electronic prescription for the medication for the patient based upon the precursor data, where the precursor data comprises an identifier for a medication that is to be prescribed to the patient and an electronic signature for a healthcare worker who is prescribing the medication, and further where the server EHR causes the electronic prescription to be routed to a first pharmacy device of a first pharmacy, where the electronic prescription includes at least one refill, and further where the electronic prescription is filled by the first pharmacy;

receiving an identifier for the electronic prescription and an identifier for a second pharmacy from a client patient portal application executing on a patient computing device that is in communication with the server patient portal application by way of a network;

transmitting the identifier for the electronic prescription and the identifier for the second pharmacy to the server EHR application, where the server EHR application:

executes a search over a computer-readable data store that comprises electronic prescriptions for a plurality of patients to identify the prescription;

determines a number of refills remaining on the electronic prescription responsive to identifying the electronic prescription;

in response to determining the number of refills remaining on the electronic prescription, constructs a second electronic prescription based upon the electronic prescription, where the second electronic prescription includes the number of refills;

constructs a second electronic prescription based upon the electronic prescription, wherein the second electronic prescription includes the number of refills;

causes a message to be received by the first pharmacy device, where the message indicates that the first pharmacy is to cease further refilling of the electronic prescription; and causes the second electronic prescription to be routed to a second pharmacy device of the second pharmacy based upon the identifier for the second pharmacy, where the second electronic prescription is filled by the second pharmacy.

9. The method of claim 8, wherein the precursor data further comprises:
an identifier for the patient;
an identifier for the healthcare worker that is prescribing the electronic prescription;
a dosage amount of the medication for the patient;
an indication as to how often the patient is to consume the medication; and
an indication of a total number of refills that are to be included in the electronic prescription.

10. The method of claim 8, wherein the precursor data fails to include an identifier for the first pharmacy.

11. The method of claim 8, further comprising transmitting identifiers for pharmacies to the client patient portal application, where the identifier for the second pharmacy is included in the identifier for the pharmacies, where the client patient portal application displays the identifiers for the pharmacies on a display of the patient computing device, and further where the client patient portal application transmits the identifier for the second pharmacy to the server patient portal application in response to receiving a selection of the identifier for the second pharmacy.

12. The method of claim 8, where, in connection with causing the second electronic prescription to be routed to the second pharmacy, the server EHR transmits the second electronic prescription to a hub application executing on a hub computing system, where the hub application routes the second electronic prescription to the second pharmacy device.

13. The method of claim 8, wherein the first electronic prescription is constructed during a first month, wherein the second electronic prescription is constructed during a second month that occurs subsequent to the first month.

14. The method of claim 8, wherein the first pharmacy device is a first fax machine or a first computing system, and the second pharmacy device is a second fax machine or a second computing system.

15. A non-transitory computer-readable medium comprising a server patient portal application that, when executed by a processor of a server computing device, causes the processor to perform acts comprising:
  transmitting precursor data for an electronic prescription for a medication for a patient to a server electronic health records application (server ERR) executing on a second server computing device, where the server EHR constructs the electronic prescription for the medication for the patient based upon the precursor data, where the precursor data comprises an identifier for a medication that is to be prescribed to the patient and an electronic signature for a healthcare worker who is prescribing the medication, and further where the server EHR causes the electronic prescription to be routed to a first pharmacy device of a first pharmacy, where the electronic prescription includes at least one refill, and further where the electronic prescription is filled by the first pharmacy;
  receiving an identifier for the electronic prescription and an identifier for a second pharmacy from a client patient portal application executing on a patient computing device that is in communication with the server patient portal application by way of a network;
  transmitting the identifier for the electronic prescription and the identifier for the second pharmacy to the server EHR application, where the server EHR application:
    executes a search over a computer-readable data store that comprises electronic prescriptions for a plurality of patients to identify the prescription;
    determines a number of refills remaining on the electronic prescription responsive to identifying the electronic prescription;
    in response to determining the number of refills remaining on the electronic prescription, constructs a second electronic prescription based upon the electronic prescription, where the second electronic prescription includes the number of refills;
    constructs a second electronic prescription based upon the electronic prescription, wherein the second electronic prescription includes the number of refills;
    causes a message to be received by the first pharmacy device, where the message indicates that the first pharmacy is to cease further refilling of the electronic prescription; and
    causes the second electronic prescription to be routed to a second pharmacy device of the second pharmacy based upon the identifier for the second pharmacy, where the second electronic prescription is filled by the second pharmacy.

16. The non-transitory computer-readable medium of claim 15, wherein the precursor data further comprises:
  an identifier for the patient;
  an identifier for the healthcare worker that is prescribing the electronic prescription;
  a dosage amount of the medication for the patient;
  an indication as to how often the patient is to consume the medication; and
  an indication of a total number of refills that are to be included in the electronic prescription.

17. The non-transitory computer-readable medium of claim 15, wherein the precursor data fails to include an identifier for the first pharmacy.

18. The non-transitory computer-readable medium of claim 15, the acts further comprising transmitting identifiers for pharmacies to the client patient portal application, where the identifier for the second pharmacy is included in the identifier for the pharmacies, where the client patient portal application displays the identifiers for the pharmacies on a display of the patient computing device, and further where the client patient portal application transmits the identifier for the second pharmacy to the server patient portal application in response to receiving a selection of the identifier for the second pharmacy.

19. The non-transitory computer-readable medium of claim 15, where, in connection with causing the second electronic prescription to be routed to the second pharmacy, the server EHR transmits the second electronic prescription to a hub application executing on a hub computing system, where the hub application routes the second electronic prescription to the second pharmacy device.

20. The non-transitory computer-readable medium of claim 15, wherein the first electronic prescription is constructed during a first month, wherein the second electronic prescription is constructed during a second month that occurs subsequent to the first month.

* * * * *